United States Patent
Cao et al.

(10) Patent No.: US 10,981,813 B2
(45) Date of Patent: Apr. 20, 2021

(54) IMPLEMENTATION METHOD FOR ELIMINATING HARMFUL ALGAL BLOOMS THROUGH OPTIMIZED UTILIZATION OF MODIFIED CLAYS

(71) Applicant: INSTITUTE OF OCEANOLOGY, CHINESE ACADEMY OF SCIENCES, Shandong (CN)

(72) Inventors: Xihua Cao, Shandong (CN); Zhiming Yu, Shandong (CN); Xiuxian Song, Shandong (CN); Yongquan Yuan, Shandong (CN); Zaixing Wu, Shandong (CN); Liyan He, Shandong (CN)

(73) Assignee: INSTITUTE OF OCEANOLOGY, CHINESE ACADEMY OF SCIENCES, Shandong (CN)

( * ) Notice: Subject to any disclaimer, the term of this patent is extended or adjusted under 35 U.S.C. 154(b) by 349 days.

(21) Appl. No.: 16/108,971

(22) Filed: Aug. 22, 2018

(65) Prior Publication Data

US 2018/0362375 A1 Dec. 20, 2018

Related U.S. Application Data (63) Continuation-in-part of application No. PCT/CN2017/106623, filed on Oct. 18, 2017.

(30) Foreign Application Priority Data

Dec. 21, 2016 (CN) .......................... 201611191048.0

(51) Int. Cl.
*C02F 1/52* (2006.01)
*C02F 3/10* (2006.01)
(Continued)

(52) U.S. Cl.
CPC ............ *C02F 3/107* (2013.01); *C02F 1/5209* (2013.01); *C02F 1/5245* (2013.01);
(Continued)

(58) Field of Classification Search
CPC ....................................................... C02F 3/107
See application file for complete search history.

(56) References Cited

U.S. PATENT DOCUMENTS

| | | | |
|---|---|---|---|
| 7,758,752 B2* | 7/2010 | Pan ......................... | C02F 1/288 210/602 |
| 2013/0335731 A1* | 12/2013 | Jorden ............... | G01N 15/0227 356/73 |
| 2017/0248568 A1* | 8/2017 | Yizhack .................. | G01J 3/42 |

FOREIGN PATENT DOCUMENTS

| | | |
|---|---|---|
| CN | 101229933 A | 7/2008 |
| CN | 101385912 A | 3/2009 |

(Continued)

OTHER PUBLICATIONS

Hendee, J.C., "An Environmental Information Synthesizer for Expert Systems: A Framework for Use in Near Real-Time Detection of Harmful Algal Blooms", Proceedings of the 17th International Conference of The Coastal Society, Dec. 31, 2000.

(Continued)

*Primary Examiner* — Peter Keyworth
(74) *Attorney, Agent, or Firm* — Novick, Kim & Lee, PLLC; Allen Xue (57) ABSTRACT

A method for eliminating harmful algal blooms through optimized utilization of a modified clay method includes building a real-time state index and a standardized value grading system for eliminating a site harmful algal bloom or a harmful algal bloom in accordance with the features of monitored harmful algal bloom organisms and modified clay flocculates; acquiring corresponding grade codes of feature index values of the harmful algal bloom in a to-be-treated (Continued)

water body or harmful algal bloom elimination effect through the real-time site state index and the standardized value grading system; comparing the above grade codes with an expert system to obtain an operation solution for eliminating harmful algal blooms through optimized utilization of the modified clay method. The result is tracked and monitored in real time and the operation solution is optimized and adjusted in time according to the harmful algal bloom elimination effect.

6 Claims, 1 Drawing Sheet

(51) Int. Cl.
*G01N 33/18* (2006.01)
*G06Q 10/04* (2012.01)
*C02F 103/00* (2006.01)
*C02F 1/68* (2006.01)
*C02F 103/08* (2006.01)

(52) U.S. Cl.
CPC ......... *G01N 33/1826* (2013.01); *G06Q 10/04* (2013.01); *C02F 1/5236* (2013.01); *C02F 1/5263* (2013.01); *C02F 1/688* (2013.01); *C02F 2103/007* (2013.01); *C02F 2103/08* (2013.01); *C02F 2209/105* (2013.01); *C02F 2209/36* (2013.01)

(56) References Cited

FOREIGN PATENT DOCUMENTS

| CN | 102495875 A | 6/2012 |
| CN | 104211151 A | 12/2014 |
| CN | 201520279270.0 U | 10/2015 |
| CN | 106709603 A | 5/2017 |

OTHER PUBLICATIONS

Gu, Zhongbo, "Study on the Ecology, Economy and Management of Red Tide Disaster and its Integrated Control", Science-Engineering (A), China Doctoral Dissertations Full-Text Database, 2011 No. 06, Dec. 31, 2000.

Xihua Cao et al., "Field Experiment and Emergent Application of Modified Clays for Phaeocystis Globosa Blooms Mitigation", Oceanologia et Limnologia Sinica, vol. 48, No. 4, Jul. 2017.

* cited by examiner

IMPLEMENTATION METHOD FOR ELIMINATING HARMFUL ALGAL BLOOMS THROUGH OPTIMIZED UTILIZATION OF MODIFIED CLAYS

CROSS-REFERENCE TO RELATED APPLICATIONS

The instant application is a continuation-in-part application of PCT international application No. PCT/CN2017/106623, filed on Oct. 18, 2017, which claims the benefit of the Chinese patent application No. CN201611191048.0, filed on Dec. 21, 2016, the entire disclosures of which are hereby incorporated by reference.

TECHNICAL FIELD

The present invention relates to the field of treating harmful algal blooms in a water environment, and particularly relates to an implementation method for eliminating harmful algal blooms through optimized utilization of modified clays.

BACKGROUND

In recent decades, harmful algal blooms (HABs) occur frequently in coastal waters, estuaries and other sensitive waters. Some poisonous and harmful algal blooms seriously influence the water quality and ecological safety, and even may directly endanger resident health. To protect the safety of the coastal environment and guarantee the healthy development of marine economy especially in some water conservation areas, culture zones, scenic spots and other sensitive waters threatened or directly affected by HABs, some counter-measures which can reduce or eliminate the hazard of HABs are urgently needed.

The modified clay method is patented technology for treating HABs. The basic principle of this technology is to aggregate bloomed algal cells by modified clay particles to form bigger particles which then subside by gravity and separate from the above water body, so as to remove the redundant bloomed algae. The treatment of HABs by the modified clay method has been improved and widely applied in the last decade. Recently, in different waters from north to south in China, there are many implementation cases in which modified clays have been applied successfully to control harmful algal blooms. Therefore, the modified clay method is considered to be the most effective and feasible counter-measure for HABs control, and receives extensive attention both in China and abroad. When the modified clay method is used for prevention and control of HABs, usually a slurry of the modified clay is pre-mixed and then sprinkled to the surface of the water body in which harmful algal bloom occurs. The modified clay particles are quickly flocculated with the bloomed algal cells and settle together so as to eliminate the excessive harmful algae. Because HABs often influence large-area waters when they outbreak, to rapidly and effectively control the dispersal of the bloomed algae, mechanized equipment operation is more effective means. Patent CN101229933 invented a device which is independent of additional motorized mixer and can be easily used to carry out the field work of the modified clay sprinkling. Patent ZL201520279270.0 provided a compositive device which can finish the whole processes of HAB treated with the modified clays. All these invented technologies aimed to promote the mechanization of field works for treating HABs.

However, the complexity and variability of HABs bring many challenges to the engineering application of the modified clay. Due to the joint effects of biological and physical influences, some bloomed algae often in homogenously scatter in the field water. Because the flocculation efficiency between the modified clay and the HAB organism is one of the key processes which determine the algal removal efficiency, the sprinkling operation manners must be adjusted frequently to bring about efficient flocculation. At present, the field application is still manually adopted for the wide range of HABs, which needs high labor power and costs high dosage of the modified clay, but only brings unsatisfactory removal efficiency. In order to ensure the effectiveness and accuracy of treatment, there is an urgent need to build a set of scientific and workable field implementation method to ease the field application and save the input of materials and manpower.

SUMMARY

The purpose of the present invention is to provide an implementation method for eliminating harmful algal blooms through optimized utilization of modified clays.

To achieve the above purpose, the present invention adopts the following technical solution:

An implementation method for eliminating harmful algal blooms through optimized utilization of modified clays is as follows:

1) building a real-time state index of algae and floc particles formed between algae and modified clays and a standardized value grading system for HAB treatment in accordance with the features of blooms and flocculation monitored in field (see Table 1);

2) obtaining the corresponding grade code which denotes the field algal bloom state by checking a standardized value grading system according to the state index values;

3) comparing the above grade code with an expert system (see Table 2) to obtain an optimized operation solution for HAB treatment with the modified clays (see Table 3).

After 20-30 min when a field operation is implemented in accordance with the introduced solution obtained by above programme, the chlorophyll fluorescence and the floc size in the treated water are determined. The preliminary effectiveness of treatment is judged according to the change of the chlorophyll fluorescence. If the chlorophyll fluorescence value is reduced by more than 15%, the field operation is continuously implemented in accordance with the introduced operation solution until the removal efficiency is less than 15%. If the chlorophyll fluorescence value is reduced by less than 15%, it means that the introduced operation solution is not ideally effective and a new solution should be chosen according to the real-time observation result using the above expert system again.

The above real-time optimized operation solution for bloomed water treatment is based on the rapid and continuous data acquisition of the relevant characteristics of the HAB-causing organisms and the modified clay flocs in water by some physical, chemical or biologic method. The acquisition methods may be off-line sample analysis or on-line continuous measurement, while on-line continuous measurement is preferred.

The above expert system is composed of three parts, i.e. HABs characteristics, modified clay floc features and operation solution for sprinkling modified clay. The HABs characteristics consist of the HAB species, distribution, strength, density, etc. The modified clay floc features consist of size distribution and concentration of the flocs formed between the bloomed algae and the modified clay particles. The operation solution is an integrated operation technology of the modified clay sprinkling which gives details for the sprinkling manners, concentration, frequency, etc.

The real-time state index and the standardized value grading system are designed by grading the index values after calculating the values of all indices of the HAB and the modified clay flocs in water. The HAB indices comprise seriousness, distribution characteristics, cell morphology, cell size, and motion capability of bloomed organisms; and the feature of the modified clay flocs is represented by the grain size of the modified clay flocs (see Table 1).

The HAB seriousness is graded into low, medium and high and their corresponding codes are L, M and H, wherein low seriousness means that the chl.a concentration given by the fluorescence of the bloomed water is less than 15 ug/L; medium seriousness means that the chl.a concentration given by the fluorescence of the bloomed water is 15-30 μg/L; high seriousness means that the chl.a concentration given by the fluorescence of the water is greater than 30 μg/L;

the HABs distribution characteristics are classified into three types, i.e. fragmentary dispersion, strip type, dense cover, with corresponding codes of D, C and G respectively. HABs usually behave differently according to the local water current or tide;

the cell morphology of the bloomed organisms are divided into spherical or non-spherical forms, with the corresponding codes of S and N. The spherical or subsphaeroidal shape is dominant in bloomed species. If there are hard bulges or subsidiary organelle on the cell outside but their sizes to the cell in diameter is less than ½, the organism is thought as sphere. Otherwise, the organism is thought as non-spherical cell;

the cell size of algae are divided into small, medium and large, and corresponding codes are L, M and N, wherein small size means that the cell diameter of the organism is less than 15 μm; medium size means that the cell diameter of the organism is 15-100 μm; and large size means that the cell diameter of the organism is greater than 100 um;

the motion capability of the organisms is divided into low, medium and high, and corresponding codes are L, M and H, wherein low capability means that the organism does not have motion capability and is suspended under the action of the water flow, etc.; medium capability means that the organism does not have motion capability but is suspended due to phototaxis or has weak buoyant capability; high capability means that the harmful algal bloom organism has strong buoyant capability;

the grain sizes of the modified clay flocs are divided into small, medium and large, and corresponding codes are L, M and H, wherein small grain size means that the median particle size (D50) is less than the cell diameter of the organism; medium grain size means that the median particle size (D50) is 1-5 times of the cell diameter of the organism; and large grain size means that the median particle size (D50) is more than 5 times of the cell diameter of the organism.

The above mentioned characteristics of the organisms can be used to describe or measure the size and density of the bloomed algae, as well as the distribution styles of the occurred HABs, such as water mass type, dispersion type, etc. The common measuring methods include a fluorescence method, a counting method, a spectrophotometric method, chromatography, etc. to quickly acquire the features of the bloomed organisms in the water, such as the size and density, as well as distribution styles of the occurred HABs. The features of the algae are observed preferably based on the on-line in vivo fluorescence method.

The above features of the modified clay flocs can be analyzed by particle size, concentration, etc. The common measuring methods include the optical online monitoring methods, micrographic methods, gravimetric methods, etc. to quickly acquire morphology features of the flocs, such as the particle size, particle concentration, particle size distribution, etc. An on-line laser light scattering method is preferred.

The order of corresponding grade codes is consistent with the order of the determined feature indexes of the HAB and the modified clay flocs.

The operation solution achieves the purpose of optimizing the effect by adjusting the sprinkling modes, density, frequency, etc. of the modified clay, wherein the sprinkling modes include raining type, pouring type, ploughing type, etc., and the raining type is preferred; the sprinkling density is a proportion of the modified clay powder with seawater in a slurry which is selected in field and obtained by premixing the powder with seawater before sprinkling onto the bloomed water surface; and the sprinkling frequency means duration time, an interval and sprinkling number of times when operation at the same site.

TABLE 1

Real-Time Site State Index and Standardized Value Grading Table

| Feature Index | Features of Harmful algal blooms or Flocs | Grades | Codes |
|---|---|---|---|
| HAB seriousness | chl.a concentration given by the fluorescence of the bloomed water is less than 15 μg/L | Low | L |
| | chl.a concentration given by the fluorescence of the bloomed water is 15-30 μg/L | Medium | M |
| | chl.a concentration given by the fluorescence of the bloomed water is greater than 30 μg/L | High | H |
| HAB distribution features | HAB presents fragmentary dispersion in a target sea area | | D |
| | HAB presents strip type and moves with water flow or tides | | C |
| | HAB presents dense cover in a target sea area with insufficient flow of water flows | | G |
| Individual forms of the bloomed organisms | Dominant organism cells of the HAB are spherical or subsphaeroidal; no hard bulge or hard subsidiary organelle with a cell diameter that is greater than ½ exists on the periphery | Spherical | S |
| | Dominant organism cells of the HAB have forms beyond the above spherical or subsphaeroidal forms | Non-spherical | N |

TABLE 1-continued

Real-Time Site State Index and Standardized Value Grading Table

| Feature Index | Features of Harmful algal blooms or Flocs | Grades | Codes |
|---|---|---|---|
| Individual sizes of the bloomed organisms | Cell diameter of the bloomed organism is less than 15 μm | Small | L |
| | Cell diameter of the bloomed organism is 15-100 μm | Medium | M |
| | Cell diameter of the bloomed organism is greater than 100 μm | Large | H |
| Motion capability of bloomed organisms | The bloomed organism does not have motion capability and is suspended under the action of the water flow, etc | Low | L |
| | The bloomed organism does not have motion capability but is suspended due to phototaxis or has weak buoyant capability | Medium | M |
| | The bloomed organism has strong buoyant capability | High | H |
| Particle size of modified clay flocs | The median particle size (D50) is less than the cell diameter of the bloomed organism | Small | L |
| | The median particle size (D50) is 1-5 times of the cell diameter of the bloomed organism | Medium | M |
| | The median particle size (D50) is more than 5 times of the cell diameter of the bloomed organism | Large | H |

TABLE 2

Expert Cognition and Decision Table for Eliminating Harmful algal blooms through Modified Clay Method

| | | | Harmful algal bloom features | | | | | Adjustment of Operation Solution Based on Features of Flocculate | | |
|---|---|---|---|---|---|---|---|---|---|---|
| No. | Codes | Seriousness | Distribution features | Individual forms | Individual sizes | Motion capability | Proposed operation solution | Particle size | Alternative solution 1 | Alternative solution 2 |
| 001 | BLDSSL | Low | Fragmentary dispersion | Spherical | Small | Low | CHLM | Small | CHLH | CHMH |
| 002 | BLDSSL | Low | Fragmentary dispersion | Spherical | Small | Low | CHLM | Medium | CHMM | CHHM |
| 003 | BLDSSL | Low | Fragmentary dispersion | Spherical | Small | Low | CHLM | Large | CHML | CHHM |
| 004 | BLDSLM | Low | Fragmentary dispersion | Spherical | Small | Medium | CHMM | Small | CHMH | CHMH |
| 005 | BLDSLM | Low | Fragmentary dispersion | Spherical | Small | Medium | CHMM | Medium | CHHM | CHHH |
| 006 | BLDSLM | Low | Fragmentary dispersion | Spherical | Small | Medium | CHMM | Large | CHML | CHHL |
| 007 | BLDSLH | Low | Fragmentary dispersion | Spherical | Small | High | CHHM | Small | CHHH | CHHH |
| 008 | BLDSLH | Low | Fragmentary dispersion | Spherical | Small | High | CHHM | Medium | CHHH | CHHH |
| 009 | BLDSLH | Low | Fragmentary dispersion | Spherical | Small | High | CHHM | Large | CHHH | CHHH |
| 010 | BLDSML | Low | Fragmentary dispersion | Spherical | Medium | Low | CHLM | Small | CHLH | CHMH |
| 011 | BLDSML | Low | Fragmentary dispersion | Spherical | Medium | Low | CHLM | Medium | CHMM | CHHM |
| 012 | BLDSML | Low | Fragmentary dispersion | Spherical | Medium | Low | CHLM | Large | CHML | CHMM |
| 013 | BLDSMM | Low | Fragmentary dispersion | Spherical | Medium | Medium | CHMM | Small | CHHH | CHHH |
| 014 | BLDSMM | Low | Fragmentary dispersion | Spherical | Medium | Medium | CHMM | Medium | CHHH | CHHH |
| 015 | BLDSMM | Low | Fragmentary dispersion | Spherical | Medium | Medium | CHMM | Large | CHHL | CHHM |
| 016 | BLDSMH | Low | Fragmentary dispersion | Spherical | Medium | High | CHHM | Small | CHHH | CHHH |
| 017 | BLDSMH | Low | Fragmentary dispersion | Spherical | Medium | High | CHHM | Medium | CHHH | CHHH |
| 018 | BLDSMH | Low | Fragmentary dispersion | Spherical | Medium | High | CHHM | Large | CHHL | CHHL |
| 019 | BLDSHL | Low | Fragmentary dispersion | Spherical | Large | Low | CHLL | Small | CHLM | CHMM |
| 020 | BLDSHL | Low | Fragmentary dispersion | Spherical | Large | Low | CHLL | Medium | CHML | CHMM |
| 021 | BLDSHL | Low | Fragmentary dispersion | Spherical | Large | Low | CHLL | Large | CHLL | CHLL |

TABLE 2-continued

Expert Cognition and Decision Table for Eliminating Harmful algal blooms through Modified Clay Method

| | | | Harmful algal bloom features | | | | | Adjustment of Operation Solution Based on Features of Flocculate | | |
|---|---|---|---|---|---|---|---|---|---|---|
| No. | Codes | Seriousness | Distribution features | Individual forms | Individual sizes | Motion capability | Proposed operation solution | Particle size | Alternative solution 1 | Alternative solution 2 |
| 022 | BLDSHM | Low | Fragmentary dispersion | Spherical | Large | Medium | CHML | Small | CHMM | CHHM |
| 023 | BLDSHM | Low | Fragmentary dispersion | Spherical | Large | Medium | CHML | Medium | CHHL | CHMM |
| 024 | BLDSHM | Low | Fragmentary dispersion | Spherical | Large | Medium | CHML | Large | CHLL | CHLL |
| 025 | BLDSHH | Low | Fragmentary dispersion | Spherical | Large | High | CHHL | Small | CHMM | CHHM |
| 026 | BLDSHH | Low | Fragmentary dispersion | Spherical | Large | High | CHHL | Medium | CHHM | CHHM |
| 027 | BLDSHH | Low | Fragmentary dispersion | Spherical | Large | High | CHHL | Large | CHML | CHLL |
| 028 | BLDNLL | Low | Fragmentary dispersion | Non-spherical | Small | Low | CHLL | Small | CHLM | CHMM |
| 029 | BLDNLL | Low | Fragmentary dispersion | Non-spherical | Small | Low | CHLL | Medium | CHML | CHMM |
| 030 | BLDNLL | Low | Fragmentary dispersion | Non-spherical | Small | Low | CHLL | Large | CHLL | CHLL |
| 031 | BLDNLM | Low | Fragmentary dispersion | Non-spherical | Small | Medium | CHML | Small | CHMM | CHHH |
| 032 | BLDNLM | Low | Fragmentary dispersion | Non-spherical | Small | Medium | CHML | Medium | CHMM | CHHH |
| 033 | BLDNLM | Low | Fragmentary dispersion | Non-spherical | Small | Medium | CHML | Large | CHLL | CHLL |
| 034 | BLDNLH | Low | Fragmentary dispersion | Non-spherical | Small | High | CHMM | Small | CHMH | CHHH |
| 035 | BLDNLH | Low | Fragmentary dispersion | Non-spherical | Small | High | CHMM | Medium | CHHH | CHHH |
| 036 | BLDNLH | Low | Fragmentary dispersion | Non-spherical | Small | High | CHMM | Large | CHML | CHLL |
| 037 | BLDNML | Low | Fragmentary dispersion | Non-spherical | Medium | Low | CHLL | Small | CHLM | CHMM |
| 038 | BLDNML | Low | Fragmentary dispersion | Non-spherical | Medium | Low | CHLL | Medium | CHLM | CHMM |
| 039 | BLDNML | Low | Fragmentary dispersion | Non-spherical | Medium | Low | CHLL | Large | CHLL | CHLL |
| 040 | BLDNMM | Low | Fragmentary dispersion | Non-spherical | Medium | Medium | CHLM | Small | CHLH | CHMH |
| 041 | BLDNMM | Low | Fragmentary dispersion | Non-spherical | Medium | Medium | CHLM | Medium | CHMM | CHMH |
| 042 | BLDNMM | Low | Fragmentary dispersion | Non-spherical | Medium | Medium | CHLM | Large | CHLL | CHLL |
| 043 | BLDNMH | Low | Fragmentary dispersion | Non-spherical | Medium | High | CHMH | Small | CHHH | CHHH |
| 044 | BLDNMH | Low | Fragmentary dispersion | Non-spherical | Medium | High | CHMH | Medium | CHHH | CHHH |
| 045 | BLDNMH | Low | Fragmentary dispersion | Non-spherical | Medium | High | CHMH | Large | CHMM | CHML |
| 046 | BLDNHL | Low | Fragmentary dispersion | Non-spherical | Large | Low | CHLL | Small | CHLM | CHMM |
| 047 | BLDNHL | Low | Fragmentary dispersion | Non-spherical | Large | Low | CHLL | Medium | CHML | CHMM |
| 048 | BLDNHL | Low | Fragmentary dispersion | Non-spherical | Large | Low | CHLL | Large | CHLL | CHLM |
| 049 | BLDNHM | Low | Fragmentary dispersion | Non-spherical | Large | Medium | CHML | Small | CHMM | CHHH |
| 050 | BLDNHM | Low | Fragmentary dispersion | Non-spherical | Large | Medium | CHML | Medium | CHMM | CHHH |
| 051 | BLDNHM | Low | Fragmentary dispersion | Non-spherical | Large | Medium | CHML | Large | CHLL | CHLL |
| 052 | BLDNHH | Low | Fragmentary dispersion | Non-spherical | Large | High | CHHL | Small | CHHM | CHMH |
| 053 | BLDNHH | Low | Fragmentary dispersion | Non-spherical | Large | High | CHHL | Medium | CHMM | CHHH |
| 054 | BLDNHH | Low | Fragmentary dispersion | Non-spherical | Large | High | CHHL | Large | CHML | CHMM |
| 055 | BLCSLL | Low | Strip type | Spherical | Small | Low | CPLM | Small | CPLH | CPMM |
| 056 | BLCSLL | Low | Strip type | Spherical | Small | Low | CPLM | Medium | CPMM | CPMH |
| 057 | BLCSLL | Low | Strip type | Spherical | Small | Low | CPLM | Large | CPLL | CPML |
| 058 | BLCSLM | Low | Strip type | Spherical | Small | Medium | CPHM | Small | CPHH | CPHH |
| 059 | BLCSLM | Low | Strip type | Spherical | Small | Medium | CPHM | Medium | CPHH | CPHH |

TABLE 2-continued

Expert Cognition and Decision Table for Eliminating Harmful algal blooms through Modified Clay Method

| | | Harmful algal bloom features | | | | | Adjustment of Operation Solution Based on Features of Flocculate | | |
|---|---|---|---|---|---|---|---|---|---|
| No. | Codes | Seriousness | Distribution features | Individual forms | Individual sizes | Motion capability | Proposed operation solution | Particle size | Alternative solution 1 | Alternative solution 2 |
| 060 | BLCSLM | Low | Strip type | Spherical | Small | Medium | CPHM | Large | CPHL | CPHH |
| 061 | BLCSLH | Low | Strip type | Spherical | Small | High | CPMH | Small | CPHH | CPHH |
| 062 | BLCSLH | Low | Strip type | Spherical | Small | High | CPMH | Medium | CPHH | CPHH |
| 063 | BLCSLH | Low | Strip type | Spherical | Small | High | CPMH | Large | CPMM | CPHM |
| 064 | BLCSML | Low | Strip type | Spherical | Medium | Low | CPLM | Small | CPLH | CPMH |
| 065 | BLCSML | Low | Strip type | Spherical | Medium | Low | CPLM | Medium | CPMM | CPHM |
| 066 | BLCSML | Low | Strip type | Spherical | Medium | Low | CPLM | Large | CPLL | CPML |
| 067 | BLCSMM | Low | Strip type | Spherical | Medium | Medium | CPMM | Small | CPMH | CPHH |
| 068 | BLCSMM | Low | Strip type | Spherical | Medium | Medium | CPMM | Medium | CPHM | CPHH |
| 069 | BLCSMM | Low | Strip type | Spherical | Medium | Medium | CPMM | Large | CPML | CPHL |
| 070 | BLCSMH | Low | Strip type | Spherical | Medium | High | CPHM | Small | CPHH | CPHH |
| 071 | BLCSMH | Low | Strip type | Spherical | Medium | High | CPHM | Medium | CPHH | CPHH |
| 072 | BLCSMH | Low | Strip type | Spherical | Medium | High | CPHM | Large | CPMM | CPHL |
| 073 | BLCSHL | Low | Strip type | Spherical | Large | Low | CPLM | Small | CPLH | CPMM |
| 074 | BLCSHL | Low | Strip type | Spherical | Large | Low | CPLM | Medium | CPMM | CPMH |
| 075 | BLCSHL | Low | Strip type | Spherical | Large | Low | CPLM | Large | CPLL | CPML |
| 076 | BLCSHM | Low | Strip type | Spherical | Large | Medium | CPHL | Small | CPHM | CPMM |
| 077 | BLCSHM | Low | Strip type | Spherical | Large | Medium | CPHL | Medium | CPMM | CPHM |
| 078 | BLCSHM | Low | Strip type | Spherical | Large | Medium | CPHL | Large | CPML | CPLL |
| 079 | BLCSHH | Low | Strip type | Spherical | Large | High | CPHL | Small | CPMM | CPMH |
| 080 | BLCSHH | Low | Strip type | Spherical | Large | High | CPHL | Medium | CPHM | CPMM |
| 081 | BLCSHH | Low | Strip type | Spherical | Large | High | CPHL | Large | CPML | CPLL |
| 082 | BLCNLL | Low | Strip type | Non-spherical | Small | Low | CPLL | Small | CPLM | CPMM |
| 083 | BLCNLL | Low | Strip type | Non-spherical | Small | Low | CPLL | Medium | CPML | CPMM |
| 084 | BLCNLL | Low | Strip type | Non-spherical | Small | Low | CPLL | Large | CPML | CPHL |
| 085 | BLCNLM | Low | Strip type | Non-spherical | Small | Medium | CPLM | Small | CPLH | CPMH |
| 086 | BLCNLM | Low | Strip type | Non-spherical | Small | Medium | CPLM | Medium | CPMM | CPHM |
| 087 | BLCNLM | Low | Strip type | Non-spherical | Small | Medium | CPLM | Large | CPML | CPHL |
| 088 | BLCNLH | Low | Strip type | Non-spherical | Small | High | CPLH | Small | CPMH | CPHH |
| 089 | BLCNLH | Low | Strip type | Non-spherical | Small | High | CPLH | Medium | CPMH | CPHH |
| 090 | BLCNLH | Low | Strip type | Non-spherical | Small | High | CPLH | Large | CPMM | CPHM |
| 091 | BLCNML | Low | Strip type | Non-spherical | Medium | Low | CPLL | Small | CPLM | CPMM |
| 092 | BLCNML | Low | Strip type | Non-spherical | Medium | Low | CPLL | Medium | CPML | CPMM |
| 093 | BLCNML | Low | Strip type | Non-spherical | Medium | Low | CPLL | Large | CPML | CPML |
| 094 | BLCNMM | Low | Strip type | Non-spherical | Medium | Medium | CPLM | Small | CPLH | CPMH |
| 095 | BLCNMM | Low | Strip type | Non-spherical | Medium | Medium | CPLM | Medium | CPMM | CPMH |
| 096 | BLCNMM | Low | Strip type | Non-spherical | Medium | Medium | CPLM | Large | CPML | CPHL |
| 097 | BLCNMH | Low | Strip type | Non-spherical | Medium | High | CPLH | Small | CPLM | CPMH |
| 098 | BLCNMH | Low | Strip type | Non-spherical | Medium | High | CPLH | Medium | CPMH | CPMM |
| 099 | BLCNMH | Low | Strip type | Non-spherical | Medium | High | CPLH | Large | CPML | CPMM |
| 100 | BLCNHL | Low | Strip type | Non-spherical | Large | Low | CPLL | Small | CPMM | CPMH |
| 101 | BLCNHL | Low | Strip type | Non-spherical | Large | Low | CPLL | Medium | CPMM | CPMH |
| 102 | BLCNHL | Low | Strip type | Non-spherical | Large | Low | CPLL | Large | CPML | CPHL |
| 103 | BLCNHM | Low | Strip type | Non-spherical | Large | Medium | CPLM | Small | CPLH | CPMH |
| 104 | BLCNHM | Low | Strip type | Non-spherical | Large | Medium | CPLM | Medium | CPMM | CPHM |
| 105 | BLCNHM | Low | Strip type | Non-spherical | Large | Medium | CPLM | Large | CPML | CPMM |

TABLE 2-continued

Expert Cognition and Decision Table for Eliminating Harmful algal blooms through Modified Clay Method

| | | | Harmful algal bloom features | | | | | Adjustment of Operation Solution Based on Features of Flocculate | | |
|---|---|---|---|---|---|---|---|---|---|---|
| No. | Codes | Seriousness | Distribution features | Individual forms | Individual sizes | Motion capability | Proposed operation solution | Particle size | Alternative solution 1 | Alternative solution 2 |
| 106 | BLCNHH | Low | Strip type | Non-spherical | Large | High | CPLH | Small | CPMH | CPHH |
| 107 | BLCNHH | Low | Strip type | Non-spherical | Large | High | CPLH | Medium | CPMH | CPHH |
| 108 | BLCNHH | Low | Strip type | Non-spherical | Large | High | CPLH | Large | CPMH | CPHM |
| 109 | BLGSLL | Low | Dense cover | Spherical | Small | Low | CFLH | Small | CFLM | CFMM |
| 110 | BLGSLL | Low | Dense cover | Spherical | Small | Low | CFLH | Medium | CFMH | CFHH |
| 111 | BLGSLL | Low | Dense cover | Spherical | Small | Low | CFLH | Large | CFMM | CFHM |
| 112 | BLGSLM | Low | Dense cover | Spherical | Small | Medium | CFMH | Small | CFHH | CFHH |
| 113 | BLGSLM | Low | Dense cover | Spherical | Small | Medium | CFMH | Medium | CFHH | CFHH |
| 114 | BLGSLM | Low | Dense cover | Spherical | Small | Medium | CFMH | Large | CFMM | CFHM |
| 115 | BLGSLH | Low | Dense cover | Spherical | Small | High | CFHH | Small | CFHH | CFHH |
| 116 | BLGSLH | Low | Dense cover | Spherical | Small | High | CFHH | Medium | CFHH | CFHH |
| 117 | BLGSLH | Low | Dense cover | Spherical | Small | High | CFHH | Large | CFHM | CFHL |
| 118 | BLGSML | Low | Dense cover | Spherical | Medium | Low | CFLM | Small | CFMM | CFHM |
| 119 | BLGSML | Low | Dense cover | Spherical | Medium | Low | CFLM | Medium | CFMM | CFMH |
| 120 | BLGSML | Low | Dense cover | Spherical | Medium | Low | CFLM | Large | CFMM | CFML |
| 121 | BLGSMM | Low | Dense cover | Spherical | Medium | Medium | CFMM | Small | CFMH | CFHH |
| 122 | BLGSMM | Low | Dense cover | Spherical | Medium | Medium | CFMM | Medium | CFHM | CFHH |
| 123 | BLGSMM | Low | Dense cover | Spherical | Medium | Medium | CFMM | Large | CFHL | CFHM |
| 124 | BLGSMH | Low | Dense cover | Spherical | Medium | High | CFHM | Small | CFHH | CFHH |
| 125 | BLGSMH | Low | Dense cover | Spherical | Medium | High | CFHM | Medium | CFHH | CFHH |
| 126 | BLGSMH | Low | Dense cover | Spherical | Medium | High | CFHM | Large | CFML | CFHL |
| 127 | BLGSHL | Low | Dense cover | Spherical | Large | Low | CFLM | Small | CFLH | CFMH |
| 128 | BLGSHL | Low | Dense cover | Spherical | Large | Low | CFLM | Medium | CFMM | CFHM |
| 129 | BLGSHL | Low | Dense cover | Spherical | Large | Low | CFLM | Large | CFML | CFHL |
| 130 | BLGSHM | Low | Dense cover | Spherical | Large | Medium | CFHL | Small | CFHM | CFHH |
| 131 | BLGSHM | Low | Dense cover | Spherical | Large | Medium | CFHL | Medium | CFHM | CFHH |
| 132 | BLGSHM | Low | Dense cover | Spherical | Large | Medium | CFHL | Large | CFML | CFLL |
| 133 | BLGSHH | Low | Dense cover | Spherical | Large | High | CFHL | Small | CFHM | CFHH |
| 134 | BLGSHH | Low | Dense cover | Spherical | Large | High | CFHL | Medium | CFHM | CFHH |
| 135 | BLGSHH | Low | Dense cover | Spherical | Large | High | CFHL | Large | CFML | CFLL |
| 136 | BLGNLL | Low | Dense cover | Non-spherical | Small | Low | CFLL | Small | CFLM | CFMH |
| 137 | BLGNLL | Low | Dense cover | Non-spherical | Small | Low | CFLL | Medium | CFMM | CFHM |
| 138 | BLGNLL | Low | Dense cover | Non-spherical | Small | Low | CFLL | Large | CFML | CFHL |
| 139 | BLGNLM | Low | Dense cover | Non-spherical | Small | Medium | CFLM | Small | CFLH | CFMH |
| 140 | BLGNLM | Low | Dense cover | Non-spherical | Small | Medium | CFLM | Medium | CFML | CFMM |
| 141 | BLGNLM | Low | Dense cover | Non-spherical | Small | Medium | CFLM | Large | CFML | CFHL |
| 142 | BLGNLH | Low | Dense cover | Non-spherical | Small | High | CFLH | Small | CFMH | CFHH |
| 143 | BLGNLH | Low | Dense cover | Non-spherical | Small | High | CFLH | Medium | CFMH | CFMM |
| 144 | BLGNLH | Low | Dense cover | Non-spherical | Small | High | CFLH | Large | CFMM | CFML |
| 145 | BLGNML | Low | Dense cover | Non-spherical | Medium | Low | CFLL | Small | CFLM | CFMH |
| 146 | BLGNML | Low | Dense cover | Non-spherical | Medium | Low | CFLL | Medium | CFML | CFMM |
| 147 | BLGNML | Low | Dense cover | Non-spherical | Medium | Low | CFLL | Large | CFML | CFHL |
| 148 | BLGNMM | Low | Dense cover | Non-spherical | Medium | Medium | CFLM | Small | CFLH | CFMH |
| 149 | BLGNMM | Low | Dense cover | Non-spherical | Medium | Medium | CFLM | Medium | CFMM | CFMH |
| 150 | BLGNMM | Low | Dense cover | Non-spherical | Medium | Medium | CFLM | Large | CFLL | CFML |
| 151 | BLGNMH | Low | Dense cover | Non-spherical | Medium | High | CFLH | Small | CFMH | CFHH |
| 152 | BLGNMH | Low | Dense cover | Non-spherical | Medium | High | CFLH | Medium | CFMH | CFHH |
| 153 | BLGNMH | Low | Dense cover | Non-spherical | Medium | High | CFLH | Large | CFML | CFHL |
| 154 | BLGNHL | Low | Dense cover | Non-spherical | Large | Low | CFLL | Small | CFLM | CFMM |

TABLE 2-continued

Expert Cognition and Decision Table for Eliminating Harmful algal blooms through Modified Clay Method

| | | | Harmful algal bloom features | | | | | Adjustment of Operation Solution Based on Features of Flocculate | | |
|---|---|---|---|---|---|---|---|---|---|---|
| No. | Codes | Seriousness | Distribution features | Individual forms | Individual sizes | Motion capability | Proposed operation solution | Particle size | Alternative solution 1 | Alternative solution 2 |
| 155 | BLGNHL | Low | Dense cover | Non-spherical | Large | Low | CFLL | Medium | CFLM | CFMM |
| 156 | BLGNHL | Low | Dense cover | Non-spherical | Large | Low | CFLL | Large | CFML | CFML |
| 157 | BLGNHM | Low | Dense cover | Non-spherical | Large | Medium | CFLM | Small | CFLH | CFMH |
| 158 | BLGNHM | Low | Dense cover | Non-spherical | Large | Medium | CFLM | Medium | CFMM | CFHM |
| 159 | BLGNHM | Low | Dense cover | Non-spherical | Large | Medium | CFLM | Large | CFLL | CFML |
| 160 | BLGNHH | Low | Dense cover | Non-spherical | Large | High | CFLH | Small | CFMH | CFHH |
| 161 | BLGNHH | Low | Dense cover | Non-spherical | Large | High | CFLH | Medium | CFMH | CFHH |
| 162 | BLGNHH | Low | Dense cover | Non-spherical | Large | High | CFLH | Large | CFLM | CFMM |
| 163 | BMDSLL | Medium | Fragmentary dispersion | Spherical | Small | Low | CHLM | Small | CHLH | CHMH |
| 164 | BMDSLL | Medium | Fragmentary dispersion | Spherical | Small | Low | CHLM | Medium | CHMM | CHHM |
| 165 | BMDSLL | Medium | Fragmentary dispersion | Spherical | Small | Low | CHLM | Large | CHML | CHHL |
| 166 | BMDSLM | Medium | Fragmentary dispersion | Spherical | Small | Medium | CHMM | Small | CHMH | CHHH |
| 167 | BMDSLM | Medium | Fragmentary dispersion | Spherical | Small | Medium | CHMM | Medium | CHHM | CHHH |
| 168 | BMDSLM | Medium | Fragmentary dispersion | Spherical | Small | Medium | CHMM | Large | CHML | CHLL |
| 169 | BMDSLH | Medium | Fragmentary dispersion | Spherical | Small | High | CHHM | Small | CHHH | CHHH |
| 170 | BMDSLH | Medium | Fragmentary dispersion | Spherical | Small | High | CHHM | Medium | CHHH | CHHH |
| 171 | BMDSLH | Medium | Fragmentary dispersion | Spherical | Small | High | CHHM | Large | CHML | CHMM |
| 172 | BMDSML | Medium | Fragmentary dispersion | Spherical | Medium | Low | CHLM | Small | CHLH | CHMH |
| 173 | BMDSML | Medium | Fragmentary dispersion | Spherical | Medium | Low | CHLM | Medium | CHMM | CHHM |
| 174 | BMDSML | Medium | Fragmentary dispersion | Spherical | Medium | Low | CHLM | Large | CHLL | CHML |
| 175 | BMDSMM | Medium | Fragmentary dispersion | Spherical | Medium | Medium | CHMM | Small | CHMH | CHHH |
| 176 | BMDSMM | Medium | Fragmentary dispersion | Spherical | Medium | Medium | CHMM | Medium | CHHM | CHHH |
| 177 | BMDSMM | Medium | Fragmentary dispersion | Spherical | Medium | Medium | CHMM | Large | CHML | CHLL |
| 178 | BMDSMH | Medium | Fragmentary dispersion | Spherical | Medium | High | CHHM | Small | CHHH | CHHH |
| 179 | BMDSMH | Medium | Fragmentary dispersion | Spherical | Medium | High | CHHM | Medium | CHHH | CHHH |
| 180 | BMDSMH | Medium | Fragmentary dispersion | Spherical | Medium | High | CHHM | Large | CHHL | CHML |
| 181 | BMDSHL | Medium | Fragmentary dispersion | Spherical | Large | Low | CHLL | Small | CHLM | CHMM |
| 182 | BMDSHL | Medium | Fragmentary dispersion | Spherical | Large | Low | CHLL | Medium | CHLM | CHMM |
| 183 | BMDSHL | Medium | Fragmentary dispersion | Spherical | Large | Low | CHLL | Large | CHML | CHHL |
| 184 | BMDSHM | Medium | Fragmentary dispersion | Spherical | Large | Medium | CHML | Small | CHMM | CHMH |
| 185 | BMDSHM | Medium | Fragmentary dispersion | Spherical | Large | Medium | CHML | Medium | CHMM | CHHM |
| 186 | BMDSHM | Medium | Fragmentary dispersion | Spherical | Large | Medium | CHML | Large | CHHL | CHLL |
| 187 | BMDSHH | Medium | Fragmentary dispersion | Spherical | Large | High | CHHL | Small | CHHM | CHHH |
| 188 | BMDSHH | Medium | Fragmentary dispersion | Spherical | Large | High | CHHL | Medium | CHHM | CHHH |
| 189 | BMDSHH | Medium | Fragmentary dispersion | Spherical | Large | High | CHHL | Large | CHML | CHLL |

TABLE 2-continued

Expert Cognition and Decision Table for Eliminating Harmful algal blooms through Modified Clay Method

| | | | Harmful algal bloom features | | | | Proposed operation solution | Adjustment of Operation Solution Based on Features of Flocculate | | |
|---|---|---|---|---|---|---|---|---|---|---|
| No. | Codes | Seriousness | Distribution features | Individual forms | Individual sizes | Motion capability | | Particle size | Alternative solution 1 | Alternative solution 2 |
| 190 | BMDNLL | Medium | Fragmentary dispersion | Non-spherical | Small | Low | CHLL | Small | CHLH | CHMM |
| 191 | BMDNLL | Medium | Fragmentary dispersion | Non-spherical | Small | Low | CHLL | Medium | CHLM | CHMM |
| 192 | BMDNLL | Medium | Fragmentary dispersion | Non-spherical | Small | Low | CHLL | Large | CHML | CHHL |
| 193 | BMDNLM | Medium | Fragmentary dispersion | Non-spherical | Small | Medium | CHML | Small | CHMM | CHMH |
| 194 | BMDNLM | Medium | Fragmentary dispersion | Non-spherical | Small | Medium | CHML | Medium | CHMM | CHHM |
| 195 | BMDNLM | Medium | Fragmentary dispersion | Non-spherical | Small | Medium | CHML | Large | CHHL | CHLL |
| 196 | BMDNLH | Medium | Fragmentary dispersion | Non-spherical | Small | High | CHMM | Small | CHMH | CHHH |
| 197 | BMDNLH | Medium | Fragmentary dispersion | Non-spherical | Small | High | CHMM | Medium | CHMH | CHHH |
| 198 | BMDNLH | Medium | Fragmentary dispersion | Non-spherical | Small | High | CHMM | Large | CHML | CHHL |
| 199 | BMDNML | Medium | Fragmentary dispersion | Non-spherical | Medium | Low | CHLL | Small | CHLM | CHMM |
| 200 | BMDNML | Medium | Fragmentary dispersion | Non-spherical | Medium | Low | CHLL | Medium | CHML | CHMM |
| 201 | BMDNML | Medium | Fragmentary dispersion | Non-spherical | Medium | Low | CHLL | Large | CHML | CHHL |
| 202 | BMDNMM | Medium | Fragmentary dispersion | Non-spherical | Medium | Medium | CHLM | Small | CHLH | CHMH |
| 203 | BMDNMM | Medium | Fragmentary dispersion | Non-spherical | Medium | Medium | CHLM | Medium | CHLH | CHMH |
| 204 | BMDNMM | Medium | Fragmentary dispersion | Non-spherical | Medium | Medium | CHLM | Large | CHML | CHHL |
| 205 | BMDNMH | Medium | Fragmentary dispersion | Non-spherical | Medium | High | CHMH | Small | CHHH | CHHH |
| 206 | BMDNMH | Medium | Fragmentary dispersion | Non-spherical | Medium | High | CHMH | Medium | CHHH | CHLH |
| 207 | BMDNMH | Medium | Fragmentary dispersion | Non-spherical | Medium | High | CHMH | Large | CHMM | CHML |
| 208 | BMDNHL | Medium | Fragmentary dispersion | Non-spherical | Large | Low | CHLL | Small | CHLM | CHMM |
| 209 | BMDNHL | Medium | Fragmentary dispersion | Non-spherical | Large | Low | CHLL | Medium | CHLM | CHMM |
| 210 | BMDNHL | Medium | Fragmentary dispersion | Non-spherical | Large | Low | CHLL | Large | CHML | CHHL |
| 211 | BMDNHM | Medium | Fragmentary dispersion | Non-spherical | Large | Medium | CHML | Small | CHMM | CHMH |
| 212 | BMDNHM | Medium | Fragmentary dispersion | Non-spherical | Large | Medium | CHML | Medium | CHMM | CHHM |
| 213 | BMDNHM | Medium | Fragmentary dispersion | Non-spherical | Large | Medium | CHML | Large | CHLL | CHHL |
| 214 | BMDNHH | Medium | Fragmentary dispersion | Non-spherical | Large | High | CHHL | Small | CHHM | CHHH |
| 215 | BMDNHH | Medium | Fragmentary dispersion | Non-spherical | Large | High | CHHL | Medium | CHHM | CHHH |
| 216 | BMDNHH | Medium | Fragmentary dispersion | Non-spherical | Large | High | CHHL | Large | CHML | CHLL |
| 217 | BMCSLL | Medium | Strip type | Spherical | Small | Low | CPLM | Small | CPLH | CPMH |
| 218 | BMCSLL | Medium | Strip type | Spherical | Small | Low | CPLM | Medium | CPLH | CPMH |
| 219 | BMCSLL | Medium | Strip type | Spherical | Small | Low | CPLM | Large | CPLL | CPML |
| 220 | BMCSLM | Medium | Strip type | Spherical | Small | Medium | CPHM | Small | CPMH | CPHH |
| 221 | BMCSLM | Medium | Strip type | Spherical | Small | Medium | CPHM | Medium | CPHH | CPHH |
| 222 | BMCSLM | Medium | Strip type | Spherical | Small | Medium | CPHM | Large | CPML | CPHL |
| 223 | BMCSLH | Medium | Strip type | Spherical | Small | High | CPMH | Small | CPHH | CPHH |
| 224 | BMCSLH | Medium | Strip type | Spherical | Small | High | CPMH | Medium | CPHH | CPHH |
| 225 | BMCSLH | Medium | Strip type | Spherical | Small | High | CPMH | Large | CPML | CPMM |
| 226 | BMCSML | Medium | Strip type | Spherical | Medium | Low | CPLM | Small | CPLH | CPMH |
| 227 | BMCSML | Medium | Strip type | Spherical | Medium | Low | CPLM | Medium | CPMM | CPHM |
| 228 | BMCSML | Medium | Strip type | Spherical | Medium | Low | CPLM | Large | CPLL | CPML |
| 229 | BMCSMM | Medium | Strip type | Spherical | Medium | Medium | CPMM | Small | CPMH | CPHH |
| 230 | BMCSMM | Medium | Strip type | Spherical | Medium | Medium | CPMM | Medium | CPHM | CPHH |
| 231 | BMCSMM | Medium | Strip type | Spherical | Medium | Medium | CPMM | Large | CPML | CPLL |
| 232 | BMCSMH | Medium | Strip type | Spherical | Medium | High | CPHM | Small | CPHH | CPMH |
| 233 | BMCSMH | Medium | Strip type | Spherical | Medium | High | CPHM | Medium | CPHH | CPHH |

TABLE 2-continued

Expert Cognition and Decision Table for Eliminating Harmful algal blooms through Modified Clay Method

| | | Harmful algal bloom features | | | | | Proposed operation solution | Adjustment of Operation Solution Based on Features of Flocculate | | |
|---|---|---|---|---|---|---|---|---|---|---|
| No. | Codes | Seriousness | Distribution features | Individual forms | Individual sizes | Motion capability | | Particle size | Alternative solution 1 | Alternative solution 2 |
| 234 | BMCSMH | Medium | Strip type | Spherical | Medium | High | CPHM | Large | CPHL | CPML |
| 235 | BMCSHL | Medium | Strip type | Spherical | Large | Low | CPLM | Small | CPLH | CPMH |
| 236 | BMCSHL | Medium | Strip type | Spherical | Large | Low | CPLM | Medium | CPMM | CPHM |
| 237 | BMCSHL | Medium | Strip type | Spherical | Large | Low | CPLM | Large | CPLL | CPML |
| 238 | BMCSHM | Medium | Strip type | Spherical | Large | Medium | CPHL | Small | CPHM | CPHH |
| 239 | BMCSHM | Medium | Strip type | Spherical | Large | Medium | CPHL | Medium | CPHM | CPMH |
| 240 | BMCSHM | Medium | Strip type | Spherical | Large | Medium | CPHL | Large | CPML | CPLL |
| 241 | BMCSHH | Medium | Strip type | Spherical | Large | High | CPHL | Small | CPHM | CPMH |
| 242 | BMCSHH | Medium | Strip type | Spherical | Large | High | CPHL | Medium | CPHM | CPMM |
| 243 | BMCSHH | Medium | Strip type | Spherical | Large | High | CPHL | Large | CPLL | CPML |
| 244 | BMCNLL | Medium | Strip type | Non-spherical | Small | Low | CPLL | Small | CPLM | CPLH |
| 245 | BMCNLL | Medium | Strip type | Non-spherical | Small | Low | CPLL | Medium | CPML | CPMM |
| 246 | BMCNLL | Medium | Strip type | Non-spherical | Small | Low | CPLL | Large | CPML | CPHL |
| 247 | BMCNLM | Medium | Strip type | Non-spherical | Small | Medium | CPLM | Small | CPLH | CPMH |
| 248 | BMCNLM | Medium | Strip type | Non-spherical | Small | Medium | CPLM | Medium | CPMM | CPHM |
| 249 | BMCNLM | Medium | Strip type | Non-spherical | Small | Medium | CPLM | Large | CPLL | CPML |
| 250 | BMCNLH | Medium | Strip type | Non-spherical | Small | High | CPLH | Small | CPLM | CPMM |
| 251 | BMCNLH | Medium | Strip type | Non-spherical | Small | High | CPLH | Medium | CPMH | CPHM |
| 252 | BMCNLH | Medium | Strip type | Non-spherical | Small | High | CPLH | Large | CPMM | CPHL |
| 253 | BMCNML | Medium | Strip type | Non-spherical | Medium | Low | CPLL | Small | CPLM | CPLH |
| 254 | BMCNML | Medium | Strip type | Non-spherical | Medium | Low | CPLL | Medium | CPLM | CPMM |
| 255 | BMCNML | Medium | Strip type | Non-spherical | Medium | Low | CPLL | Large | CPML | CPHL |
| 256 | BMCNMM | Medium | Strip type | Non-spherical | Medium | Medium | CPLM | Small | CPLH | CPMH |
| 257 | BMCNMM | Medium | Strip type | Non-spherical | Medium | Medium | CPLM | Medium | CPMM | CPHM |
| 258 | BMCNMM | Medium | Strip type | Non-spherical | Medium | Medium | CPLM | Large | CPLL | CPML |
| 259 | BMCNMH | Medium | Strip type | Non-spherical | Medium | High | CPLH | Small | CPMH | CPHH |
| 260 | BMCNMH | Medium | Strip type | Non-spherical | Medium | High | CPLH | Medium | CPMH | CPHH |
| 261 | BMCNMH | Medium | Strip type | Non-spherical | Medium | High | CPLH | Large | CPLM | CPML |
| 262 | BMCNHL | Medium | Strip type | Non-spherical | Large | Low | CPLL | Small | CPLM | CPMH |
| 263 | BMCNHL | Medium | Strip type | Non-spherical | Large | Low | CPLL | Medium | CPML | CPHL |
| 264 | BMCNHL | Medium | Strip type | Non-spherical | Large | Low | CPLL | Large | CPML | CPHL |
| 265 | BMCNHM | Medium | Strip type | Non-spherical | Large | Medium | CPLM | Small | CPLH | CPMH |
| 266 | BMCNHM | Medium | Strip type | Non-spherical | Large | Medium | CPLM | Medium | CPMM | CPHM |
| 267 | BMCNHM | Medium | Strip type | Non-spherical | Large | Medium | CPLM | Large | CPLL | CPML |
| 268 | BMCNHH | Medium | Strip type | Non-spherical | Large | High | CPLH | Small | CPMH | CPHH |
| 269 | BMCNHH | Medium | Strip type | Non-spherical | Large | High | CPLH | Medium | CPMH | CPHH |
| 270 | BMCNHH | Medium | Strip type | Non-spherical | Large | High | CPLH | Large | CPMM | CPHM |
| 271 | BMGSLL | Medium | Dense cover | Spherical | Small | Low | CFLH | Small | CFMH | CFHH |
| 272 | BMGSLL | Medium | Dense cover | Spherical | Small | Low | CFLH | Medium | CFMH | CFHH |
| 273 | BMGSLL | Medium | Dense cover | Spherical | Small | Low | CFLH | Large | CFML | CFMM |
| 274 | BMGSLM | Medium | Dense cover | Spherical | Small | Medium | CFMH | Small | CFHH | CFHH |
| 275 | BMGSLM | Medium | Dense cover | Spherical | Small | Medium | CFMH | Medium | CFHH | CFHH |
| 276 | BMGSLM | Medium | Dense cover | Spherical | Small | Medium | CFMH | Large | CFML | CFHM |
| 277 | BMGSLH | Medium | Dense cover | Spherical | Small | High | CFHH | Small | CFHH | CFHH |

TABLE 2-continued

Expert Cognition and Decision Table for Eliminating Harmful algal blooms through Modified Clay Method

| | | | Harmful algal bloom features | | | | Proposed operation solution | Adjustment of Operation Solution Based on Features of Flocculate | | |
|---|---|---|---|---|---|---|---|---|---|---|
| No. | Codes | Seriousness | Distribution features | Individual forms | Individual sizes | Motion capability | | Particle size | Alternative solution 1 | Alternative solution 2 |
| 278 | BMGSLH | Medium | Dense cover | Spherical | Small | High | CFHH | Medium | CFHH | CFHH |
| 279 | BMGSLH | Medium | Dense cover | Spherical | Small | High | CFHH | Large | CFHM | CFHL |
| 280 | BMGSML | Medium | Dense cover | Spherical | Medium | Low | CFLM | Small | CFLH | CFMH |
| 281 | BMGSML | Medium | Dense cover | Spherical | Medium | Low | CFLM | Medium | CFMM | CFHM |
| 282 | BMGSML | Medium | Dense cover | Spherical | Medium | Low | CFLM | Large | CFLL | CFML |
| 283 | BMGSMM | Medium | Dense cover | Spherical | Medium | Medium | CFMM | Small | CFMH | CFMH |
| 284 | BMGSMM | Medium | Dense cover | Spherical | Medium | Medium | CFMM | Medium | CFHM | CFHH |
| 285 | BMGSMM | Medium | Dense cover | Spherical | Medium | Medium | CFMM | Large | CFML | CFHL |
| 286 | BMGSMH | Medium | Dense cover | Spherical | Medium | High | CFHM | Small | CFHH | CFHH |
| 287 | BMGSMH | Medium | Dense cover | Spherical | Medium | High | CFHM | Medium | CFHH | CFHH |
| 288 | BMGSMH | Medium | Dense cover | Spherical | Medium | High | CFHM | Large | CFHL | CFML |
| 289 | BMGSHL | Medium | Dense cover | Spherical | Large | Low | CFLM | Small | CFLH | CFMH |
| 290 | BMGSHL | Medium | Dense cover | Spherical | Large | Low | CFLM | Medium | CFMM | CFMH |
| 291 | BMGSHL | Medium | Dense cover | Spherical | Large | Low | CFLM | Large | CFML | CFHL |
| 292 | BMGSHM | Medium | Dense cover | Spherical | Large | Medium | CFHL | Small | CFHM | CFHM |
| 293 | BMGSHM | Medium | Dense cover | Spherical | Large | Medium | CFHL | Medium | CFHM | CFHM |
| 294 | BMGSHM | Medium | Dense cover | Spherical | Large | Medium | CFHL | Large | CFHM | CFHM |
| 295 | BMGSHH | Medium | Dense cover | Spherical | Large | High | CFHL | Small | CFHM | CFHM |
| 296 | BMGSHH | Medium | Dense cover | Spherical | Large | High | CFHL | Medium | CFHM | CFHM |
| 297 | BMGSHH | Medium | Dense cover | Spherical | Large | High | CFHL | Large | CFML | CFML |
| 298 | BMGNLL | Medium | Dense cover | Non-spherical | Small | Low | CFLL | Small | CFLM | CFMM |
| 299 | BMGNLL | Medium | Dense cover | Non-spherical | Small | Low | CFLL | Medium | CFML | CFHL |
| 300 | BMGNLL | Medium | Dense cover | Non-spherical | Small | Low | CFLL | Large | CFML | CFHL |
| 301 | BMGNLM | Medium | Dense cover | Non-spherical | Small | Medium | CFLM | Small | CFLH | CFMH |
| 302 | BMGNLM | Medium | Dense cover | Non-spherical | Small | Medium | CFLM | Medium | CFMM | CFMH |
| 303 | BMGNLM | Medium | Dense cover | Non-spherical | Small | Medium | CFLM | Large | CFML | CFHL |
| 304 | BMGNLH | Medium | Dense cover | Non-spherical | Small | High | CFLH | Small | CFMH | CFHH |
| 305 | BMGNLH | Medium | Dense cover | Non-spherical | Small | High | CFLH | Medium | CFMH | CFHH |
| 306 | BMGNLH | Medium | Dense cover | Non-spherical | Small | High | CFLH | Large | CFLM | CFMM |
| 307 | BMGNML | Medium | Dense cover | Non-spherical | Medium | Low | CFLL | Small | CFLH | CFLM |
| 308 | BMGNML | Medium | Dense cover | Non-spherical | Medium | Low | CFLL | Medium | CFML | CFMM |
| 309 | BMGNML | Medium | Dense cover | Non-spherical | Medium | Low | CFLL | Large | CFML | CFML |
| 310 | BMGNMM | Medium | Dense cover | Non-spherical | Medium | Medium | CFLM | Small | CFLH | CFMM |
| 311 | BMGNMM | Medium | Dense cover | Non-spherical | Medium | Medium | CFLM | Medium | CFMM | CFHM |
| 312 | BMGNMM | Medium | Dense cover | Non-spherical | Medium | Medium | CFLM | Large | CFMM | CFML |
| 313 | BMGNMH | Medium | Dense cover | Non-spherical | Medium | High | CFLH | Small | CFMH | CFHH |
| 314 | BMGNMH | Medium | Dense cover | Non-spherical | Medium | High | CFLH | Medium | CFMH | CFMH |
| 315 | BMGNMH | Medium | Dense cover | Non-spherical | Medium | High | CFLH | Large | CFMM | CFHM |
| 316 | BMGNHL | Medium | Dense cover | Non-spherical | Large | Low | CFLL | Small | CFLM | CFMM |
| 317 | BMGNHL | Medium | Dense cover | Non-spherical | Large | Low | CFLL | Medium | CFML | CFMM |
| 318 | BMGNHL | Medium | Dense cover | Non-spherical | Large | Low | CFLL | Large | CFML | CFHL |
| 319 | BMGNHM | Medium | Dense cover | Non-spherical | Large | Medium | CFLM | Small | CFLH | CFHH |
| 320 | BMGNHM | Medium | Dense cover | Non-spherical | Large | Medium | CFLM | Medium | CFMM | CHMM |
| 321 | BMGNHM | Medium | Dense cover | Non-spherical | Large | Medium | CFLM | Large | CFHL | CFHM |
| 322 | BMGNHH | Medium | Dense cover | Non-spherical | Large | High | CFLH | Small | CFMH | CFHH |

TABLE 2-continued

Expert Cognition and Decision Table for Eliminating Harmful algal blooms through Modified Clay Method

| | | Harmful algal bloom features | | | | | Proposed operation solution | Adjustment of Operation Solution Based on Features of Flocculate | | |
|---|---|---|---|---|---|---|---|---|---|---|
| No. | Codes | Seriousness | Distribution features | Individual forms | Individual sizes | Motion capability | | Particle size | Alternative solution 1 | Alternative solution 2 |
| 323 | BMGNHH | Medium | Dense cover | Non-spherical | Large | High | CFLH | Medium | CFMH | CFHH |
| 324 | BMGNHH | Medium | Dense cover | Non-spherical | Large | High | CFLH | Large | CFMM | CFHM |
| 325 | BHDSLL | High | Fragmentary dispersion | Spherical | Small | Low | CHLM | Small | CHLH | CFMM |
| 326 | BHDSLL | High | Fragmentary dispersion | Spherical | Small | Low | CHLM | Medium | CHMM | CHMH |
| 327 | BHDSLL | High | Fragmentary dispersion | Spherical | Small | Low | CHLM | Large | CHMM | CHHL |
| 328 | BHDSLM | High | Fragmentary dispersion | Spherical | Small | Medium | CHMM | Small | CHMH | CHMH |
| 329 | BHDSLM | High | Fragmentary dispersion | Spherical | Small | Medium | CHMM | Medium | CHHM | CHMH |
| 330 | BHDSLM | High | Fragmentary dispersion | Spherical | Small | Medium | CHMM | Large | CHHM | CHHL |
| 331 | BHDSLH | High | Fragmentary dispersion | Spherical | Small | High | CHHM | Small | CHHH | CHHH |
| 332 | BHDSLH | High | Fragmentary dispersion | Spherical | Small | High | CHHM | Medium | CHHH | CHHH |
| 333 | BHDSLH | High | Fragmentary dispersion | Spherical | Small | High | CHHM | Large | CHHL | CHMM |
| 334 | BHDSML | High | Fragmentary dispersion | Spherical | Medium | Low | CHLM | Small | CHLH | CHMM |
| 335 | BHDSML | High | Fragmentary dispersion | Spherical | Medium | Low | CHLM | Medium | CHMM | CHHM |
| 336 | BHDSML | High | Fragmentary dispersion | Spherical | Medium | Low | CHLM | Large | CHMM | CHLL |
| 337 | BHDSMM | High | Fragmentary dispersion | Spherical | Medium | Medium | CHMM | Small | CHMH | CHHH |
| 338 | BHDSMM | High | Fragmentary dispersion | Spherical | Medium | Medium | CHMM | Medium | CHHM | CHMH |
| 339 | BHDSMM | High | Fragmentary dispersion | Spherical | Medium | Medium | CHMM | Large | CHML | CHHL |
| 340 | BHDSMH | High | Fragmentary dispersion | Spherical | Medium | High | CHHM | Small | CHHH | CHHH |
| 341 | BHDSMH | High | Fragmentary dispersion | Spherical | Medium | High | CHHM | Medium | CHHH | CHHH |
| 342 | BHDSMH | High | Fragmentary dispersion | Spherical | Medium | High | CHHM | Large | CHHL | CHML |
| 343 | BHDSHL | High | Fragmentary dispersion | Spherical | Large | Low | CHLL | Small | CHLM | CHLH |
| 344 | BHDSHL | High | Fragmentary dispersion | Spherical | Large | Low | CHLL | Medium | CHML | CHMM |
| 345 | BHDSHL | High | Fragmentary dispersion | Spherical | Large | Low | CHLL | Large | CHML | CHHL |
| 346 | BHDSHM | High | Fragmentary dispersion | Spherical | Large | Medium | CHML | Small | CHMM | CHMH |
| 347 | BHDSHM | High | Fragmentary dispersion | Spherical | Large | Medium | CHML | Medium | CHHL | CHHM |
| 348 | BHDSHM | High | Fragmentary dispersion | Spherical | Large | Medium | CHML | Large | CHHL | CHHL |
| 349 | BHDSHH | High | Fragmentary dispersion | Spherical | Large | High | CHHL | Small | CHHM | CHHH |
| 350 | BHDSHH | High | Fragmentary dispersion | Spherical | Large | High | CHHL | Medium | CHHM | CHHM |
| 351 | BHDSHH | High | Fragmentary dispersion | Spherical | Large | High | CHHL | Large | CHML | CHLL |
| 352 | BHDNLL | High | Fragmentary dispersion | Non-spherical | Small | Low | CHLL | Small | CHLM | CHLH |
| 353 | BHDNLL | High | Fragmentary dispersion | Non-spherical | Small | Low | CHLL | Medium | CHML | CHMM |
| 354 | BHDNLL | High | Fragmentary dispersion | Non-spherical | Small | Low | CHLL | Large | CHML | CHHL |
| 355 | BHDNLM | High | Fragmentary dispersion | Non-spherical | Small | Medium | CHML | Small | CHMM | CHMH |
| 356 | BHDNLM | High | Fragmentary dispersion | Non-spherical | Small | Medium | CHML | Medium | CHHL | CHHM |
| 357 | BHDNLM | High | Fragmentary dispersion | Non-spherical | Small | Medium | CHML | Large | CHHL | CHHL |

TABLE 2-continued

Expert Cognition and Decision Table for Eliminating Harmful algal blooms through Modified Clay Method

| | | Harmful algal bloom features | | | | | Adjustment of Operation Solution Based on Features of Flocculate | | |
|---|---|---|---|---|---|---|---|---|---|
| No. | Codes | Seriousness | Distribution features | Individual forms | Individual sizes | Motion capability | Proposed operation solution | Particle size | Alternative solution 1 | Alternative solution 2 |
| 358 | BHDNLH | High | Fragmentary dispersion | Non-spherical | Small | High | CHMM | Small | CHHM | CHHH |
| 359 | BHDNLH | High | Fragmentary dispersion | Non-spherical | Small | High | CHMM | Medium | CHHM | CHHM |
| 360 | BHDNLH | High | Fragmentary dispersion | Non-spherical | Small | High | CHMM | Large | CHML | CHLL |
| 361 | BHDNML | High | Fragmentary dispersion | Non-spherical | Medium | Low | CHLL | Small | CHLH | CHLM |
| 362 | BHDNML | High | Fragmentary dispersion | Non-spherical | Medium | Low | CHLL | Medium | CHML | CHMM |
| 363 | BHDNML | High | Fragmentary dispersion | Non-spherical | Medium | Low | CHLL | Large | CHML | CHHL |
| 364 | BHDNMM | High | Fragmentary dispersion | Non-spherical | Medium | Medium | CHLM | Small | CHLH | CHMH |
| 365 | BHDNMM | High | Fragmentary dispersion | Non-spherical | Medium | Medium | CHLM | Medium | CHMM | CHHM |
| 366 | BHDNMM | High | Fragmentary dispersion | Non-spherical | Medium | Medium | CHLM | Large | CHMM | CHHM |
| 367 | BHDNMH | High | Fragmentary dispersion | Non-spherical | Medium | High | CHMH | Small | CHHH | CHHH |
| 368 | BHDNMH | High | Fragmentary dispersion | Non-spherical | Medium | High | CHMH | Medium | CHHH | CHHH |
| 369 | BHDNMH | High | Fragmentary dispersion | Non-spherical | Medium | High | CHMH | Large | CHHM | CHHL |
| 370 | BHDNHL | High | Fragmentary dispersion | Non-spherical | Large | Low | CHLL | Small | CHLM | CHLH |
| 371 | BHDNHL | High | Fragmentary dispersion | Non-spherical | Large | Low | CHLL | Medium | CHML | CHMM |
| 372 | BHDNHL | High | Fragmentary dispersion | Non-spherical | Large | Low | CHLL | Large | CHML | CHHL |
| 373 | BHDNHM | High | Fragmentary dispersion | Non-spherical | Large | Medium | CHML | Small | CHMM | CHMH |
| 374 | BHDNHM | High | Fragmentary dispersion | Non-spherical | Large | Medium | CHML | Medium | CHHL | CHHM |
| 375 | BHDNHM | High | Fragmentary dispersion | Non-spherical | Large | Medium | CHML | Large | CHHL | CHMM |
| 376 | BHDNHH | High | Fragmentary dispersion | Non-spherical | Large | High | CHHL | Small | CHHM | CHHH |
| 377 | BHDNHH | High | Fragmentary dispersion | Non-spherical | Large | High | CHHL | Medium | CHHM | CHHM |
| 378 | BHDNHH | High | Fragmentary dispersion | Non-spherical | Large | High | CHHL | Large | CHMH | CHHL |
| 379 | BHCSLL | High | Strip type | Spherical | Small | Low | CPLM | Small | CPLH | CPMH |
| 380 | BHCSLL | High | Strip type | Spherical | Small | Low | CPLM | Medium | CPMM | CPLH |
| 381 | BHCSLL | High | Strip type | Spherical | Small | Low | CPLM | Large | CPML | CPMM |
| 382 | BHCSLM | High | Strip type | Spherical | Small | Medium | CPHM | Small | CPHH | CPHH |
| 383 | BHCSLM | High | Strip type | Spherical | Small | Medium | CPHM | Medium | CPHH | CPMH |
| 384 | BHCSLM | High | Strip type | Spherical | Small | Medium | CPHM | Large | CPHL | CPHL |
| 385 | BHCSLH | High | Strip type | Spherical | Small | High | CPMH | Small | CPHH | CPHH |
| 386 | BHCSLH | High | Strip type | Spherical | Small | High | CPMH | Medium | CPHH | CPHH |
| 387 | BHCSLH | High | Strip type | Spherical | Small | High | CPMH | Large | CPML | CPMM |
| 388 | BHCSML | High | Strip type | Spherical | Medium | Low | CPLM | Small | CPLH | CPMH |
| 389 | BHCSML | High | Strip type | Spherical | Medium | Low | CPLM | Medium | CPMM | CPHM |
| 390 | BHCSML | High | Strip type | Spherical | Medium | Low | CPLM | Large | CPMM | CPML |
| 391 | BHCSMM | High | Strip type | Spherical | Medium | Medium | CPMM | Small | CPMH | CPHH |
| 392 | BHCSMM | High | Strip type | Spherical | Medium | Medium | CPMM | Medium | CPMH | CPHM |
| 393 | BHCSMM | High | Strip type | Spherical | Medium | Medium | CPMM | Large | CPML | CPHL |
| 394 | BHCSMH | High | Strip type | Spherical | Medium | High | CPHM | Small | CPHH | CPMH |
| 395 | BHCSMH | High | Strip type | Spherical | Medium | High | CPHM | Medium | CPHH | CPMH |
| 396 | BHCSMH | High | Strip type | Spherical | Medium | High | CPHM | Large | CPHL | CPML |
| 397 | BHCSHL | High | Strip type | Spherical | Large | Low | CPLM | Small | CPLH | CPMH |
| 398 | BHCSHL | High | Strip type | Spherical | Large | Low | CPLM | Medium | CPLH | CPMH |
| 399 | BHCSHL | High | Strip type | Spherical | Large | Low | CPLM | Large | CPML | CPMM |
| 400 | BHCSHM | High | Strip type | Spherical | Large | Medium | CPHL | Small | CPHM | CPHH |
| 401 | BHCSHM | High | Strip type | Spherical | Large | Medium | CPHL | Medium | CPHM | CPHL |
| 402 | BHCSHM | High | Strip type | Spherical | Large | Medium | CPHL | Large | CPLL | CPML |
| 403 | BHCSHH | High | Strip type | Spherical | Large | High | CPHL | Small | CPHM | CPHH |
| 404 | BHCSHH | High | Strip type | Spherical | Large | High | CPHL | Medium | CPHM | CPMM |
| 405 | BHCSHH | High | Strip type | Spherical | Large | High | CPHL | Large | CPML | CPMM |
| 406 | BHCNLL | High | Strip type | Non-spherical | Small | Low | CPLL | Small | CPLM | CPLH |

TABLE 2-continued

Expert Cognition and Decision Table for Eliminating Harmful algal blooms through Modified Clay Method

| | | | Harmful algal bloom features | | | | Proposed | Adjustment of Operation Solution Based on Features of Flocculate | | |
|---|---|---|---|---|---|---|---|---|---|---|
| No. | Codes | Seriousness | Distribution features | Individual forms | Individual sizes | Motion capability | operation solution | Particle size | Alternative solution 1 | Alternative solution 2 |
| 407 | BHCNLL | High | Strip type | Non-spherical | Small | Low | CPLL | Medium | CPML | CPHL |
| 408 | BHCNLL | High | Strip type | Non-spherical | Small | Low | CPLL | Large | CPML | CPHL |
| 409 | BHCNLM | High | Strip type | Non-spherical | Small | Medium | CPLM | Small | CPLH | CPMH |
| 410 | BHCNLM | High | Strip type | Non-spherical | Small | Medium | CPLM | Medium | CPMM | CPHM |
| 411 | BHCNLM | High | Strip type | Non-spherical | Small | Medium | CPLM | Large | CPMM | CPML |
| 412 | BHCNLH | High | Strip type | Non-spherical | Small | High | CPLH | Small | CPMH | CPHH |
| 413 | BHCNLH | High | Strip type | Non-spherical | Small | High | CPLH | Medium | CPMH | CPHH |
| 414 | BHCNLH | High | Strip type | Non-spherical | Small | High | CPLH | Large | CPMM | CPHL |
| 415 | BHCNML | High | Strip type | Non-spherical | Medium | Low | CPLL | Small | CPLM | CPLH |
| 416 | BHCNML | High | Strip type | Non-spherical | Medium | Low | CPLL | Medium | CPML | CPMM |
| 417 | BHCNML | High | Strip type | Non-spherical | Medium | Low | CPLL | Large | CPML | CPHL |
| 418 | BHCNMM | High | Strip type | Non-spherical | Medium | Medium | CPLM | Small | CPLH | CPMH |
| 419 | BHCNMM | High | Strip type | Non-spherical | Medium | Medium | CPLM | Medium | CPMM | CPHM |
| 420 | BHCNMM | High | Strip type | Non-spherical | Medium | Medium | CPLM | Large | CPLL | CPML |
| 421 | BHCNMH | High | Strip type | Non-spherical | Medium | High | CPLH | Small | CPMH | CPHH |
| 422 | BHCNMH | High | Strip type | Non-spherical | Medium | High | CPLH | Medium | CPMH | CPHH |
| 423 | BHCNMH | High | Strip type | Non-spherical | Medium | High | CPLH | Large | CPML | CPHL |
| 424 | BHCNHL | High | Strip type | Non-spherical | Large | Low | CPLL | Small | CPLM | CPMM |
| 425 | BHCNHL | High | Strip type | Non-spherical | Large | Low | CPLL | Medium | CPMM | CPHM |
| 426 | BHCNHL | High | Strip type | Non-spherical | Large | Low | CPLL | Large | CPML | CPHL |
| 427 | BHCNHM | High | Strip type | Non-spherical | Large | Medium | CPLM | Small | CPLH | CPMM |
| 428 | BHCNHM | High | Strip type | Non-spherical | Large | Medium | CPLM | Medium | CPMM | CPMH |
| 429 | BHCNHM | High | Strip type | Non-spherical | Large | Medium | CPLM | Large | CPLL | CPML |
| 430 | BHCNHH | High | Strip type | Non-spherical | Large | High | CPLH | Small | CPMH | CPHH |
| 431 | BHCNHH | High | Strip type | Non-spherical | Large | High | CPLH | Medium | CPMH | CPHH |
| 432 | BHCNHH | High | Strip type | Non-spherical | Large | High | CPLH | Large | CPML | CPMM |
| 433 | BHGSLL | High | Dense cover | Spherical | Small | Low | CFLH | Small | CFMH | CFHH |
| 434 | BHGSLL | High | Dense cover | Spherical | Small | Low | CFLH | Medium | CFMH | CFHH |
| 435 | BHGSLL | High | Dense cover | Spherical | Small | Low | CFLH | Large | CFML | CFHL |
| 436 | BHGSLM | High | Dense cover | Spherical | Small | Medium | CFMH | Small | CFHH | CFHH |
| 437 | BHGSLM | High | Dense cover | Spherical | Small | Medium | CFMH | Medium | CFHH | CFHH |
| 438 | BHGSLM | High | Dense cover | Spherical | Small | Medium | CFMH | Large | CFLM | CFMM |
| 439 | BHGSLH | High | Dense cover | Spherical | Small | High | CFHH | Small | CFHH | CFHH |
| 440 | BHGSLH | High | Dense cover | Spherical | Small | High | CFHH | Medium | CFMH | CFMH |
| 441 | BHGSLH | High | Dense cover | Spherical | Small | High | CFHH | Large | CFML | CFMM |
| 442 | BHGSML | High | Dense cover | Spherical | Medium | Low | CFLM | Small | CFLH | CFMH |
| 443 | BHGSML | High | Dense cover | Spherical | Medium | Low | CFLM | Medium | CFMM | CFHM |
| 444 | BHGSML | High | Dense cover | Spherical | Medium | Low | CFLM | Large | CFHL | CFML |
| 445 | BHGSMM | High | Dense cover | Spherical | Medium | Medium | CFMM | Small | CFMH | CFHH |
| 446 | BHGSMM | High | Dense cover | Spherical | Medium | Medium | CFMM | Medium | CFMH | CFMH |
| 447 | BHGSMM | High | Dense cover | Spherical | Medium | Medium | CFMM | Large | CFML | CFLL |
| 448 | BHGSMH | High | Dense cover | Spherical | Medium | High | CFHM | Small | CFHH | CFMH |
| 449 | BHGSMH | High | Dense cover | Spherical | Medium | High | CFHM | Medium | CFMH | CFHH |
| 450 | BHGSMH | High | Dense cover | Spherical | Medium | High | CFHM | Large | CFML | CFHL |
| 451 | BHGSHL | High | Dense cover | Spherical | Large | Low | CFLM | Small | CFLH | CFMH |

TABLE 2-continued

Expert Cognition and Decision Table for Eliminating Harmful algal blooms through Modified Clay Method

| No. | Codes | Seriousness | Distribution features | Individual forms | Individual sizes | Motion capability | Proposed operation solution | Particle size | Alternative solution 1 | Alternative solution 2 |
|---|---|---|---|---|---|---|---|---|---|---|
| 452 | BHGSHL | High | Dense cover | Spherical | Large | Low | CFLM | Medium | CFMM | CFHM |
| 453 | BHGSHL | High | Dense cover | Spherical | Large | Low | CFLM | Large | CFMM | CFHL |
| 454 | BHGSHM | High | Dense cover | Spherical | Large | Medium | CFHL | Small | CFMH | CFHH |
| 455 | BHGSHM | High | Dense cover | Spherical | Large | Medium | CFHL | Medium | CFHM | CFHH |
| 456 | BHGSHM | High | Dense cover | Spherical | Large | Medium | CFHL | Large | CFML | CFLM |
| 457 | BHGSHH | High | Dense cover | Spherical | Large | High | CFHL | Small | CFHM | CFHH |
| 458 | BHGSHH | High | Dense cover | Spherical | Large | High | CFHL | Medium | CFHM | CFMM |
| 459 | BHGSHH | High | Dense cover | Spherical | Large | High | CFHL | Large | CFML | CFLL |
| 460 | BHGNLL | High | Dense cover | Non-spherical | Small | Low | CFLL | Small | CFLM | CFMM |
| 461 | BHGNLL | High | Dense cover | Non-spherical | Small | Low | CFLL | Medium | CFML | CFMM |
| 462 | BHGNLL | High | Dense cover | Non-spherical | Small | Low | CFLL | Large | CFML | CFHL |
| 463 | BHGNLM | High | Dense cover | Non-spherical | Small | Medium | CFLM | Small | CFLH | CFMM |
| 464 | BHGNLM | High | Dense cover | Non-spherical | Small | Medium | CFLM | Medium | CFMM | CFHM |
| 465 | BHGNLM | High | Dense cover | Non-spherical | Small | Medium | CFLM | Large | CFLL | CFML |
| 466 | BHGNLH | High | Dense cover | Non-spherical | Small | High | CFLH | Small | CFMH | CFHH |
| 467 | BHGNLH | High | Dense cover | Non-spherical | Small | High | CFLH | Medium | CFMH | CFMM |
| 468 | BHGNLH | High | Dense cover | Non-spherical | Small | High | CFLH | Large | CFML | CFHL |
| 469 | BHGNML | High | Dense cover | Non-spherical | Medium | Low | CFLL | Small | CFLM | CFMM |
| 470 | BHGNML | High | Dense cover | Non-spherical | Medium | Low | CFLL | Medium | CFML | CFMM |
| 471 | BHGNML | High | Dense cover | Non-spherical | Medium | Low | CFLL | Large | CFML | CFHL |
| 472 | BHGNMM | High | Dense cover | Non-spherical | Medium | Medium | CFLM | Small | CFLH | CFMH |
| 473 | BHGNMM | High | Dense cover | Non-spherical | Medium | Medium | CFLM | Medium | CFMM | CFMH |
| 474 | BHGNMM | High | Dense cover | Non-spherical | Medium | Medium | CFLM | Large | CFML | CFHL |
| 475 | BHGNMH | High | Dense cover | Non-spherical | Medium | High | CFLH | Small | CFMH | CFHH |
| 476 | BHGNMH | High | Dense cover | Non-spherical | Medium | High | CFLH | Medium | CFMH | CFHH |
| 477 | BHGNMH | High | Dense cover | Non-spherical | Medium | High | CFLH | Large | CFMM | CFHM |
| 478 | BHGNHL | High | Dense cover | Non-spherical | Large | Low | CFLL | Small | CFLM | CFMM |
| 479 | BHGNHL | High | Dense cover | Non-spherical | Large | Low | CFLL | Medium | CFML | CFMM |
| 480 | BHGNHL | High | Dense cover | Non-spherical | Large | Low | CFLL | Large | CFML | CFML |
| 481 | BHGNHM | High | Dense cover | Non-spherical | Large | Medium | CFLM | Small | CFMH | CFHH |
| 482 | BHGNHM | High | Dense cover | Non-spherical | Large | Medium | CFLM | Medium | CFMM | CFHM |
| 483 | BHGNHM | High | Dense cover | Non-spherical | Large | Medium | CFLM | Large | CFML | CFHL |
| 484 | BHGNHH | High | Dense cover | Non-spherical | Large | High | CFLH | Small | CFMH | CFHH |
| 485 | BHGNHH | High | Dense cover | Non-spherical | Large | High | CFLH | Medium | CFMH | CFHH |
| 486 | BHGNHH | High | Dense cover | Non-spherical | Large | High | CFLH | Large | CFMM | CFML |

Note:
The initial operation solution is the proposed operation solution which is given according to site harmful algal bloom features. After operation for 20-30 min, the grain size of the flocculate and the fluorescence value of the chlorophyll in vivo within 1 m from surface layer of the water body in the operation site are observed. If the fluorescence value of chlorophyll is reduced by above 15%, it is recommended to continue the operation in accordance with the site operation solution; and if the fluorescence value of chlorophyll is reduced by under 15%, it is considered to adjust the operation solution. When the solution is adjusted, the operation effect is firstly graded according to the observed grain size features of the flocculate (see Table 1); and then adjustable operation solutions are queried from the original harmful algal bloom code and corresponding flocculate feature lines in the table.

TABLE 3

Operation Solution for Sprinkling Modified Clay

| Codes | Sprinkling Manner | Sprinkling Strength | Sprinkling Concentration |
|---|---|---|---|
| CPLL | Pursuing and raining type | Low frequency | Low |
| CPLM | Pursuing and raining type | Low frequency | Medium |
| CPLH | Pursuing and raining type | Low frequency | High |
| CPML | Pursuing and raining type | Medium frequency | Low |
| CPMM | Pursuing and raining type | Medium frequency | Medium |
| CPMH | Pursuing and raining type | Medium frequency | High |
| CPHL | Pursuing and raining type | High frequency | Low |
| CPHM | Pursuing and raining type | High frequency | Medium |
| CPHH | Pursuing and raining type | High frequency | High |
| CHLL | Field sweeping and raining type | Low frequency | Low |
| CHLM | Field sweeping and raining type | Low frequency | Medium |
| CHLH | Field sweeping and raining type | Low frequency | High |
| CHML | Field sweeping and raining type | Medium frequency | Low |
| CHMM | Field sweeping and raining type | Medium frequency | Medium |
| CHMH | Field sweeping and raining type | Medium frequency | High |
| CHHL | Field sweeping and raining type | High frequency | Low |
| CHHM | Field sweeping and raining type | High frequency | Medium |
| CHHH | Field sweeping and raining type | High frequency | High |
| CFLL | Local centralizing and raining type | Low frequency | Low |
| CFLM | Local centralizing and raining type | Low frequency | Medium |
| CFLH | Local centralizing and raining type | Low frequency | High |
| CFML | Local centralizing and raining type | Medium frequency | Low |
| CFMM | Local centralizing and raining type | Medium frequency | Medium |
| CFMH | Local centralizing and raining type | Medium frequency | High |
| CFHL | Local centralizing and raining type | High frequency | Low |
| CFHM | Local centralizing and raining type | High frequency | Medium |
| CFHH | Local centralizing and raining type | High frequency | High |

Sprinkling strength means the number of times of repeatedly sprinkling modified clay on the same water surface in unit time. Low frequency is less than 2 times/hour, medium frequency is 2-5 times/hour and high frequency is greater than 5 times/hour.

When the harmful algal bloom is treated by the modified clay method, generally the modified clay material is mixed with seawater in a container in advance to form thin pulp with a certain concentration, and then is sprinkled on the surface of the water body of the harmful algal bloom. Sprinkling concentration means the concentration of the modified clay material premixed with seawater. Low concentration is less than 100 g/L, medium concentration is 100-200 g/L and high concentration is greater than 200 g/L. The present invention has the following advantages:

A screening method for operation solutions of eliminating harmful algal blooms through optimized utilization of a modified clay method is provided. The method proposes an optimized solution for sprinkling operation of modified clay after programmed decisions of an expert system for guiding the operation of eliminating harmful algal bloom using modified clay based on the features of the harmful algal bloom organisms and modified clay flocculates within the water body observed in site in real time, so as to improve refinement and programming during site implementation of treating the harmful algal bloom using the modified clay method, facilitating the increase of field operation efficiency of treating the harmful algal bloom using the modified clay method and providing a foundation for the development of harmful algal bloom prevention and treatment projects towards automatic construction.

Of course, the implementation method in the present invention is not only suitable for treating the harmful algal bloom using the modified clay method, but also suitable for treating the harmful algal bloom using unmodified natural clay, so as to effectively enhance energy efficiency of treating the harmful algal bloom using the clay materials.

DETAILED DESCRIPTION

Figure 1:
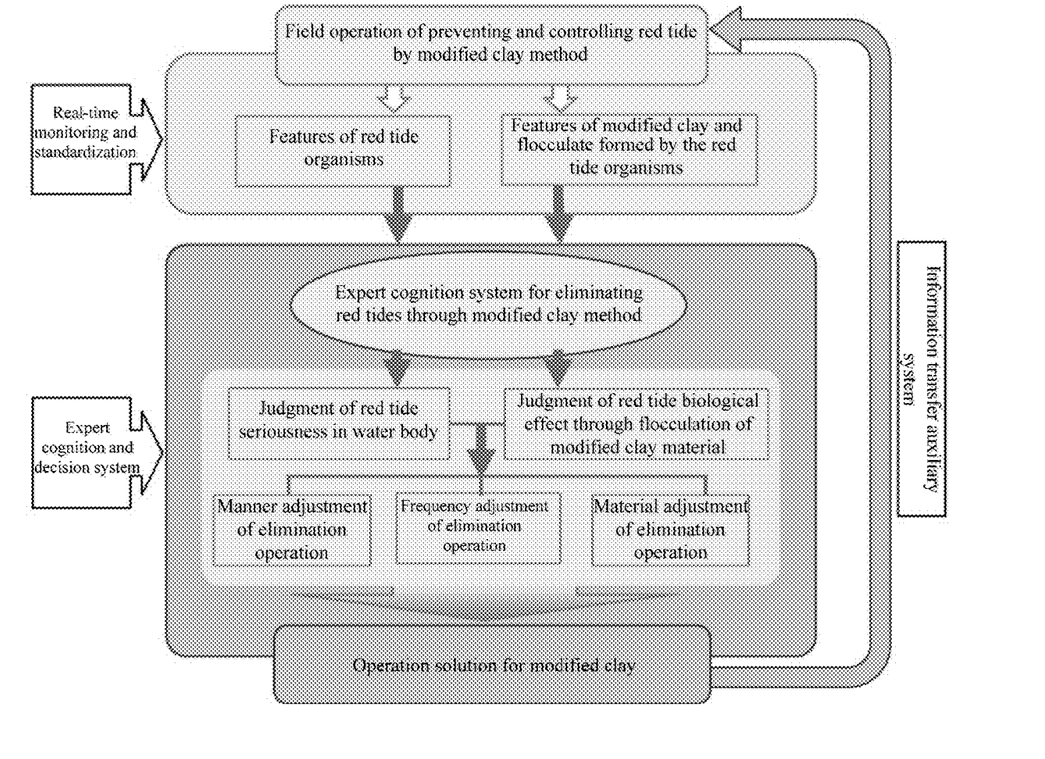
FIG. 1 is a structural diagram of guiding operation of eliminating harmful algal blooms based on an expert system provided in the embodiments of the present invention.

To make the purpose, the technical solution and the advantages of the present invention more clear, the present invention will be further described below in details through embodiments. It should be understood that concrete embodiments described for this purpose are only used to explain the present invention, not to limit the present invention.

The present invention increases algae removal efficiency of the modified clay in engineering construction through optimized utilization of the site implementation effect of eliminating the harmful algal bloom by a modified clay method. In view of the problems of work target of elimination operation, extensive use amount, etc. due to lack of a refined operation method in the existing engineering construction, the present invention provides an implementation method for eliminating harmful algal blooms through an efficient optimized modified clay method. The method proposes an optimized operation solution through programmed decisions of the expert system based on a harmful algal bloom prevention and treatment expert system having intelligent information processing capability in accordance with the feature index values of the harmful algal bloom organisms and modified clay flocculates in the water body acquired in site in real time, and adjusts the operation solution in real time according to the change of the site feature index values. The method can realize refinement and programming during site implementation of treating the harmful algal bloom using the modified clay method, and facilitates the increase of field operation efficiency of treating the harmful algal bloom using the modified clay method.

EMBODIMENTS

Heterosigma carterae of harmful algal bloom is a common harmful algal bloom organism in offshore breeding areas in China. It is found through microscopy with a microscope that cells are oval. The individual has a length of about 8-25 μm and a width of about 6-15 μm through determination with a fluorescence method, a counting method, a spectrophotometric method and chromatography. Heterosigma carterae has strong buoyant capability and often spreads over the whole sea area when the harmful algal bloom breaks out. The heterosigma carterae harmful algal bloom breaks out in a certain offshore bay in Qingdao. The fluorescence value of chlorophyll in vivo in the water body is monitored by an online in vivo fluorimeter in site, which is greater than 30 μg/L. By referring to Table 1, grading and quantifying codes of the harmful algal bloom in this area are judged as follows: serious harmful algal bloom (H), fragmentary dispersion (D), spherical cell monomer (S), small cell (L), and strong buoyant capability (H). Letter B is added before each index. The code of the heterosigma carterae harmful algal bloom is obtained as BHDSLH in accordance with the above order. A recommended elimination solution with the harmful algal bloom code of BHDSLH is queried in Table 2 as CHHM, with the number of 332. The operation solution for sprinkling modified clay of CHHM is queried in Table 3 as follows: the sprinkling manner is field sweeping and raining type; sprinkling strength is high frequency; sprinkling concentration is medium; and the solution can be adopted in site operation.

After site construction for 30 minutes, the median particle size (D50) of flocculate is measured as 45 um within 1 meter on the surface layer of the working region with an underwater laser light scattering particle detector. If the fluorescence value of the chlorophyll in vivo in the water body is reduced to a value within 25 μg/L by above 15%, the operation can be continued in accordance with the operation solution. But if the fluorescence value of the chlorophyll in vivo in the water body is still greater than 25 μg/L and is reduced by below 15%, it can be preliminarily judged that the used operation solution is not ideal in the elimination effect and needs to be adjusted in time. By referring to Table 1 for the grain size features of modified clay flocculates in which the flocculate is assessed as medium (M), and Table 3 in which the harmful algal bloom code is BHDSLH and the flocculate grade is M line, it can be queried that the recommended operation solution is adjusted as CHHH. The solution has a sprinkling manner of field sweeping and raining type, and high frequency sprinkling strength and high sprinkling concentration. Field operation can be adjusted to this operation manner.

Through site online observation and expert system decisions for guiding the operation of eliminating the harmful algal bloom using modified clay, a scientific operation solution is provided rapidly for the site elimination operation of the harmful algal bloom, and can be optimized in time according to the site implementation effect. The operation solution is especially consistent with requirements for quick response and quick effect of disaster emergency control. In addition, programming operation for treating the harmful algal bloom using the modified clay method is initiated, providing a foundation for the development of harmful algal bloom prevention and treatment projects towards automatic construction.

We claim:

1. A method for treating harmful algal blooms (HABs), comprising:
   mixing a modified clay with HABs in water to form flocs of the modified clay;
   measuring a plurality of characteristics of the HABs and the modified clay flocs, wherein the plurality of characteristics comprise a chlorophyll fluorescence of the water, a distribution of the HABs, a form of organisms in the HABs, a size of organisms in the HABs, a mobility of organisms in the HABs, and a size of the modified clay flocs;
   assigned an index value to each of the plurality of characteristics;
   comparing the index values to a standardized value grading system for HABs treatment to assign a grade code of the HABs being treated;
   comparing the grade code with an expert system according to Table 2 in the specification to select a first field operation according a first operation solution code that treats the HABs with the modified clay; and
   carrying out the first field operation.

2. The method according to claim 1, comprising:
   measuring the chlorophyll fluorescence and the size of the flocs in the water 20-30 min after the first field operation is implemented; if the chlorophyll fluorescence value is reduced by more than 15%, continuing the field operation; if the chlorophyll fluorescence value is reduced by less than 15%, selecting a second field operation according to a second operation solution code according to the expert system based on the plurality of characteristics measured after the first field operation.

3. The method according to claim 1, wherein the plurality of characteristics of the HABs and the modified clay flocs are monitored in real-time, and the standardized value grading system are designed by grading the index values after calculating all index values of the HABs and the modified clay flocs in water.

4. The method according to claim 3, wherein the index values comprises low HAB seriousness, medium HAB seriousness, and high HAB seriousness, wherein the low HAB seriousness means that the chl.a concentration given by the fluorescence of the water is less than 15 μg/L; the medium HAB seriousness means that the chl.a concentration given by the fluorescence of the water is 15-30 μg/L; the high HAB seriousness means that the chl.a concentration given by the fluorescence of the water is greater than 30 μg/L.

5. The method according to claim 1, wherein the expert system is used for acquiring the operation solution including grade codes and corresponding feature grades of the HABs organisms and providing a corresponding operation solution code.

6. The method according to claim 5, wherein the operation solution code corresponds to conditions for sprinkling the modified clay that includes sprinkling modes, and a density and frequency for sprinkling the modified clay, wherein the sprinkling modes include raining type, pouring type or ploughing type; the sprinkling density is a proportion of the modified clay powder with seawater in a slurry obtained by premixing the modified clay with seawater; and the sprinkling frequency means a number of sprinkling events, a duration of each sprinkling event, and a time interval between two adjacent sprinkling events.

* * * * *